United States Patent [19]

Bout et al.

[11] Patent Number: 4,606,219

[45] Date of Patent: Aug. 19, 1986

[54] GAS DETECTORS

[75] Inventors: Bernardus J. Bout, Walkerville; Ernest P. van Eeden, Johannesburg; Nicolaas T. van der Walt, Mondeor, all of South Africa

[73] Assignee: Crucible S.A., Luxembourg, Luxembourg

[21] Appl. No.: 625,710

[22] Filed: Jun. 28, 1984

[30] Foreign Application Priority Data

Jul. 5, 1983 [ZA] South Africa ............... 83/4894

[51] Int. Cl.[4] ............................................. G01N 27/04
[52] U.S. Cl. ......................................................... 73/23
[58] Field of Search ................ 73/23, 27 R; 340/632, 340/633, 634, 870.09; 422/94, 98

[56] References Cited

U.S. PATENT DOCUMENTS

| 1,876,706 | 9/1932 | MacCain et al. | 340/633 |
| 2,441,677 | 5/1948 | Stallsmith | 340/633 |
| 3,041,590 | 6/1962 | Lucci | 340/633 |
| 3,603,954 | 9/1971 | Takeuchi | 73/23 |
| 4,088,986 | 5/1978 | Boucher | 340/634 |
| 4,390,869 | 6/1983 | Christen et al. | 340/634 |
| 4,464,653 | 8/1984 | Winner | 340/632 |
| 4,517,161 | 5/1985 | Gravina et al. | 340/634 |

Primary Examiner—Stephen A. Kreitman
Attorney, Agent, or Firm—Kuhn Muller and Bazerman

[57] ABSTRACT

A carbon monoxide gas detector comprises a housing consisting of two enclosures 10 and 12 having ports in the wall thereof to provide a tortuous path for air entering the inner enclosure 12. A gas cell transducer 16 connected to an electrical circuit 18 provides signals indicative of gas concentration. The detector is powered from a remote supply via wires 22 and 26 and provides gas concentration signals via a wire 24 to a remote central station with a fail-safe feature wherein failure of the circuit or the detector will provide signals interpreted as dangerous gas concentrations.

10 Claims, 4 Drawing Figures

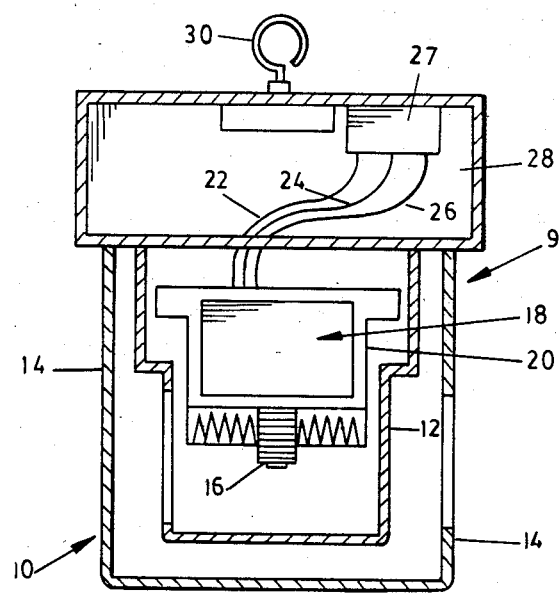
FIG_1
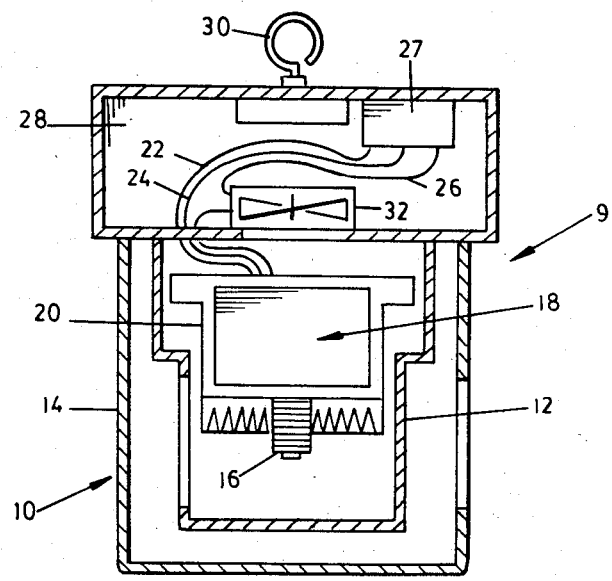
FIG_2

GAS DETECTORS

BACKGROUND OF THE INVENTION

The invention relates to gas detectors.

Gas detectors are already known including transducers which respond to the presence of one or more selected gases to change their electrical characteristics to enable, by electrically monitoring such characteristics, the detection of the presence and concentration of the selected gas in an environment. It is usual to provide an instrument having a transducer, an electrical monitoring circuit and a local electrical supply as well as a display for the instrument so that the presence and/or concentration of the selected gas or gases can be readily determined in a chosen environment. Such instruments especially when accuracy is required and low concentrations, a few part per million, are to be measured tend to be expensive and non-robust.

The present invention is concerned with providing gas detectors which are comparatively cheap and are for use in detecting low concentrations of gas particularly carbon monoxide and methane. The gas detectors of the present invention have particular although not exclusive application in detecting the presence of fires or potentially hazardous conditions in underground mine workings.

SUMMARY OF THE INVENTION

According to one aspect of the invention there is provided a gas detector which comprises a housing, a gas cell transducer mounted in the housing and responsive to change its electrical characteristics with changes of concentration of selected gas in the housing, an electrical monitoring circuit supported in the housing and coupled to the cell which is arranged to receive an electrical supply from a remote control station and to supply monitoring signal to the control station indicative of the concentration of the gas.

According to another aspect of the invention there is provided a selected gas concentration monitoring system for monitoring the presence of the gas in an environment such as the underground working of a mine, including a plurality of gas detectors, each detector comprising a gas cell transducer mounted in a housing and responsive to change its electrical characteristics with changes in concentration of the gas in the housing and an electrical monitoring circuit supported in the housing, and a control station electrically connected to each detector for providing an electrical supply thereto and for receiving monitoring signals from each detector indicative of concentrations of the gas in the respective housings.

The gas cell transducers may be arranged to respond to a single selected gas, such as carbon monoxide or methane, or may be responsive to two or more gases and mixtures thereof.

The housings of each detector may comprise an enclosure surrounding the cells having ports in the walls thereof to allow gas to enter through the ports. Preferably, such housings are so arranged that gas entering the ports is swirled slowly around the inside thereof even when the housing is in a position where an air flow is moving rapidly past the outside of the housing.

The cell transducer is preferably arranged to be easily replaceable and provided for example with a plug-in mounting. This means where the operational life of the cell transducer is short, say only several months, the cell transducer can be readily exchanged as required.

BRIEF DESCRIPTION OF THE DRAWINGS

A carbon monoxide gas detector according to the invention will now be described by way of example with reference to the accompanying drawings in which:

FIGS. 1 and 2 are sectioned elevations of two similar detectors; and

DESCRIPTION OF PREFERRED EMBODIMENTS

Figure 4:
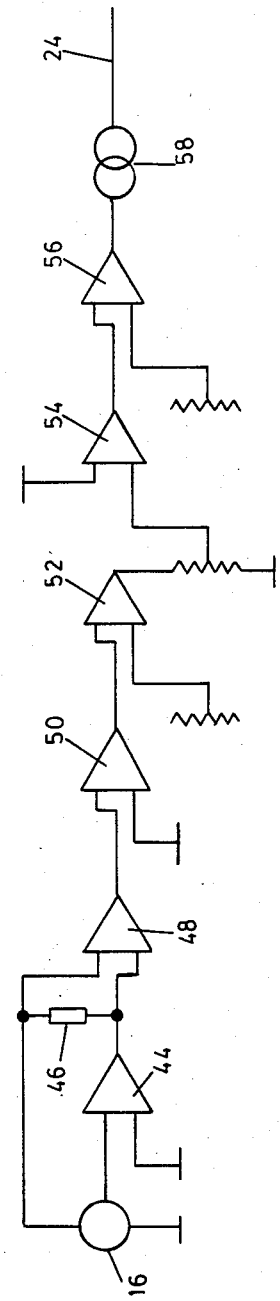
FIG. 4 is a schematic circuit diagram of the detector circuit used with the invention.

Referring to the drawing, in FIG. 1 the gas detector 9 has a housing 10 which comprises an inner enclosure 12 and an outer enclosure 14, each enclosure having six porting slots which are non-aligned with one another. This means that when air is flowing relatively rapidly past the housing 10 some of the air enters progressively into the inside of the enclosure 12 via the slots and swirls slowly there around. A gas cell transducer 16 is mounted in the enclosure 12 and responds to the presence and the concentration of carbon monoxide to change its electrical characteristics. An electronic circuit 18 is mounted and encapsulated in a chamber 20 above the transducer 16 and is electrically coupled to the transducer 16. Three wires 22, 24 and 26 are connected to the circuit 18 and to a terminal block 27.

The housing 10 has a lid 28 provided with a support eye 30 so that the detector 9 can be readily suspended at a chosen location.

In use, the detector 9 is positioned in a chosen location in underground workings and is associated with a number of like detectors at various suitable positions in a district of underground workings. All the detectors are electrically supplied from a central control station to which monitoring signals are supplied from the detectors indicative of the concentration of carbon monoxide in the region of respective detectors.

In FIG. 2, the detector is the same as the detector of FIG. 1 except that a small fan 32 is fitted inside the lid 28. The fan 32 is supplied from the station via the wire 26. The fan 32 draws air into the chamber 12 via the slots in the walls of the enclosures 12 and 14. The provision of the fan 32 enables the detector 9 to respond efficiently and rapidly to changes of carbon monoxide concentration even where the detector is mounted in a region where there is little or no air flow. Normally in mine workings, conventional forced air ventilation provides adequate circulation past the detector when it is located in or near a main airway. However, it is possible that the detector 9 is positioned in a region of relatively poor air circulation or the air ventilation may be turned off for maintenance or be inoperative due to a fault. In such cases, the fan 32 ensures that there is adequate movement of air so that air enters into the enclosure 12 to enable the transducer 16 to respond to and provide detection of carbon monoxide.

Figure 3:
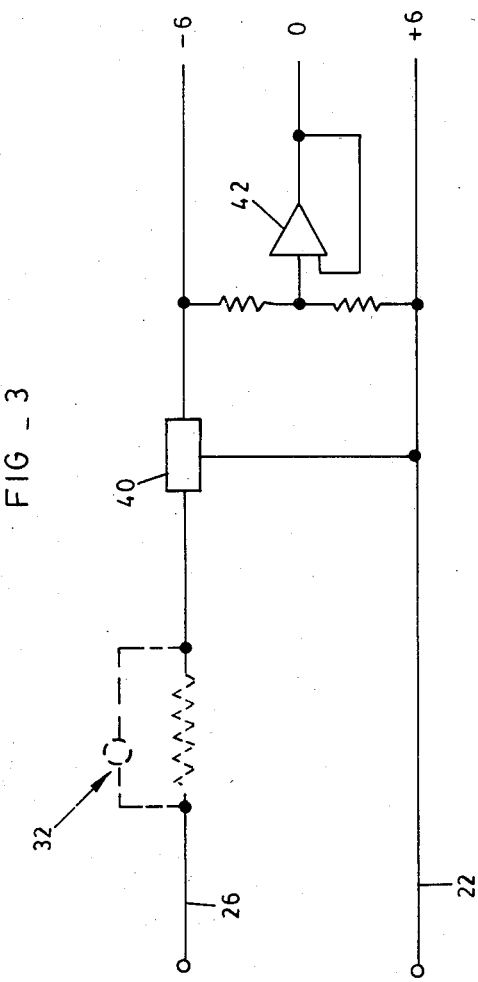
FIG. 3 is a schematic circuit diagram of the power supply circuit utilized with the invention.

In FIG. 3, the circuit includes a supply circuit which receives a −15 volt direct current supply from a central control station between lines 22 and 26. A stabilising network 40 reduces the voltage to −12 volts and supplies a divider circuit, including an amplifier 42, to provide a common zero, together with a +6 volts and a −6 volts output for the remainder of the circuit.

As seen in FIG. 4, gas cell transducer 16 is connected to a matching amplifier 44, with a resistor 46 in its feedback circuit, the output of which is connected via an amplifier 48 to a further amplifier 50 incorporating temperature correction feedback. Further amplifiers 52, 54 and 56 are connected in series to a current driver 58, the output of which is connected to the wire 24.

The inputs of the amplifiers 52 and 54 are adjustable to alter the zero setting of the circuit and the range span respectively. The input of the amplifier 56 is also adjustable to provide an off-set of the overall output of the circuit.

In the described circuit, an output for supply along the wire 24 is chosen, indicative of carbon monoxide concentration, so that when the concentration of carbon monoxide is zero, the output of the current driver 58 is one milliamp. This corresponds to a zero output at the amplifier 54 so that the off-set input of the amplifier 56 must be 1 volt.

The zero setting for the circuit is adjusted by altering an input to the amplifier 52. This adjustable input is required to balance the small current which flows through the transducer 16 when no carbon monoxide is present.

The span of detection selected is controlled or adjusted by an input to the amplifier 54 and is chosen to be zero to 100 parts per million of carbon monoxide; this span can also be adjusted if required by altering the resistance value of the resistor 46. After initial setting up of the circuit, the detector is then tested by subjecting the transducer 16 to a known concentration of carbon monoxide and the span adjusted to suit the chosen range.

Normally each of the adjustments mentioned can be carried out by the provision of suitable variable resistors which can be accessed, using a screwdriver for example, without damaging or interfering with the encapsulation of the circuit in the chamber 20.

In use, the transducer 16 which per se forms no part of the invention, responds to the presence of the carbon monoxide to change its electrical characteristics so that the inputs to the amplifier 48 become unbalanced and the output current of the current driver 58 reduces appropriately. For monitoring mine workings, the range chosen as explained is 100 parts per million so that if the concentration rises to this level the output current of the current driver 58 reduces from 1 milliamp to zero.

It will be appreciated that other circuit arrangements can be provided and also other settings used in the circuit. The use of a reducing current output as gas concentration increases is however preferred because, as would be evident to those having skill in the art, this introduces a fail-safe feature since, for example, loss of supply current to the unit would also result in the indicating device reading otherwise than full-scale deflection, which would indicate a fault. Also, where recording is made, especially by chart recorders, full-scale or maximum deflection at zero gas concentration is advantageous.

The transducer 16 is plugged into position in the housing 10. This enables the transducer 16 to be changed easily. Suitable transducers presently available have a working life of 6 to 18 months in mining environments and must therefore be replaced normally every 6 to 12 months. As will be appreciated, the described circuit enables each replaced transducer to be calibrated and the circuit adjusted when a replacement transducer is first plugged into the housing 10 and also at other times if required.

The fan 32 when fitted is connected to the wire 26 as shown dotted in FIG. 3.

As mentioned earlier the detectors are suitably positioned in chosen different locations throughout a district of underground workings; the central control station is normally and conveniently situated at the surface of the mine. At the control station it is preferable to have a number of chart recorders respectively coupled to each of the detectors to monitor the changes of concentration of carbon monoxide. The chart recorder can each be associated with an alarm circuit and arranged to provide an audible and/or visable alarm whenever the concentration rises to a predetermined level. The alarm circuit, or an additional circuit incorporated with the described electrical circuit in the encapsulation in the chamber 20 in each detector, can be provided to produce such an alarm signal. Further, the detectors or the alarm circuit at the surface may be provided with an additional circuit arrangment which responds to rates of chanqe of carbon monoxide concentration and produces a further alarm signal whenever this rate exceeds a predetermined rate.

A telemetry system can be used to communicate the magnitude of the output current of the current driver 58 to the central control station. In such a case the telemetering link is used to power the electrical circuits of the detectors as well as telemetering circuitry provided in each detector.

The monitoring of carbon monoxide is especially advantageous for detecting the on-set of an underground fire or even the presence or occurrence of fire hazardous conditions as they develop particularly in a coal mine. Although the presence of other gases, for example carbon dioxide may also be used. However occasional overall comparatively high background concentration of carbon dioxide in a mine even when there is no fire or fire hazard, means that changes indicative of a fire are not so easily distinguishable from normal safe conditions. By monitoring the presence of carbon monoxide, methane, or mixture thereof, the on-set and increase of small concentrations of such gases provides a generally much more reliable and more easily distinguishable condition on which to detect rapidly the outbreak of a fire or other hazardous conditions.

As each described detector in a system for monitoring the concentration of gas in an underground district does not require a local power source and has remote indicators, chart recorders for example, each detector can be made relatively cheaply. Further, the remote station not only readily provides an early indication of a fire but the central monitoring of the concentration of gas has the added advantage that faulty or inoperative detectors can be identified. This can be done either by observing uncharacteristic changes in their output monitoring signals or by comparing those signals with the signals supplied from detectors positioned nearby in the same district.

The system may also be used to monitor the presence or the on-set of dangerous gas concentrations either in mine or even in long roadway tunnels which need not be associated with fires or fire hazards but may be related to health hazardous conditions.

Preferably, the central monitoring station is of the type already used with ionisation type smoke detectors. Further, same housings for the detectors that are used and currently available for such smoke detectors can be advantageously used. This enables the gas detectors to be produced in bulk quantities using the same machinery as for producing the housings of the smoke detectors. Additionally, the gas detectors can be incorporated if desired into a system which monitors a number of smoke detectors and a number of carbon monoxide detectors, distributed in the same district, at the same time as may be desired.

We claim:

1. A gas detector which comprises a housing, a gas cell transducer mounted in the housing and responsive to change its electrical characteristic with changes of concentration of selected gas in the housing, an electrical monitoring circuit supported in the housing and electrically connected to the transducer which is arranged to produce monitoring signals correponding to the electrical characteristic of the transducer, and a remote control station electrically connected to the monitoring circuit which supplies power to the monitoring circuit and receives the monitoring signals indicative of the concentration of the gas, the monitoring circuit including circuit means for producing monitoring signals having a maximum value when the concentration of gas is at a predetermined minimum, and which reduce in value as the concentration of gas increases toward a predetermined maximum, so that a failure of the gas detector or an interruption in the electrical connections between the remote control station and the monitoring circuit will cause an indication at the remote control station of a dangerous gas concentration, thus providing fail-safe operation of the gas detector.

2. A gas detector according to claim 1 in which the gas cell transducer is arranged to respond to changes in carbon monoxide concentrations in the housing.

3. A gas detector according to claim 1, in which the housing comprises an enclosure surrounding the cell transducer having ports in the walls thereof to allow gas to enter through the ports.

4. A gas detector according to claim 3, in which the housing comprises two ported enclosures one inside the other and the ports in the walls of each enclosure being misaligned to provide a tortuous path for air entering into the inside of the inner enclosure which surrounds the cell transducer.

5. A gas detector according to any one of claim 1, in which the cell transducer is releasably supported in the housing.

6. A gas detector according to any one of claim 1, including an electrically driven fan mounted in the housing arranged to draw air into the detector towards the cell transducer.

7. A carbon monoxide gas detector which comprises a housing, a gas cell transducer mounted in the housing and responsive to change its electrical characteristic with changes of concentration of selected gas in the housing, an electrical monitoring circuit supported in the housing and electrically connected to the transducer which is arranged to produce monitoring signals corresponding to the electrical characteristic of the transducer, the monitoring circuit including an amplifier the output of which has a predetermined maximum value when the concentration of gas is at a predetermined-minimum, and the output of which reduces in value and approaches zero as the concentration of gas increases towards a predetermined maximum, and a remote control station electrically connected to the monitoring circuit which supplies power to the monitoring circuit and receives the monitoring signals indicative of the concentration of gas, so that a failure of the monitoring circuit, the remote control station, or the electrical connections therebetween will cause an indication at the remote control station of a dangerous gas concentration, thus providing fail-safe operation of the gas detector, the housing further comprising a first enclosure surrounding the cell transducer having ports in the walls, and a second enclosure having ports in the walls thereof to allow gas to pass through the walls, the ports of the first and second enclosure being misaligned to provide a tortuous path for air entering into the inside of the inner enclosure from outside the second enclosure.

8. A selected gas concentration monitoring system for monitoring the presence of gas in an environment such as the underground workings of a mine, including a plurality of gas detectors, each detector comprising a gas cell transducer mounted in a housing and responsive to change its electrical characteristic with changes in the concentration of the gas in the housing, and an electrical monitoring circuit supported in the housing and electrically connected to the transducer which is arranged to produced monitoring signals corresponding to the electrical characteristic of the transducer, the monitoring circuit including circuit means for producing monitoring signals having a maximum value when the concentration of gas is at a predetermined minimum, and which reduce in value as the concentration of gas increases towards a predetermined maximum, and a remote control station electrically connected to each of the monitoring circuits which provides electrical power to the monitoring circuits and receives monitoring signals from each monitoring circuit indicative of respective concentrations of gas in the housings of the respective detectors, so that a failure of any one of the gas detectors or of the electrical connections between that gas detector and the remote control station will cause an indication at the remote control station of a dangerous gas concentration in the vicinity of that gas detector, thus providing fail-safe operation of the system.

9. A gas detector according to claim 7 in which the electrical monitoring circuit further includes a current driver arranged to be driven by the amplifier, the monitoring signals provided by the monitoring circuit being current signals.

10. A gas detector according to claim 9 in which the monitoring signals are reduced in magnitude from a preset maximum current magnitude as the concentration of the gas increases above the minimum concentration.

* * * * *